United States Patent
Plaga et al.

(10) Patent No.: US 7,204,165 B1
(45) Date of Patent: Apr. 17, 2007

(54) ANTHROPOMORPHIC MANIKIN HEAD SKULL CAP LOAD MEASUREMENT DEVICE

(75) Inventors: John A. Plaga, Fairborn, OH (US); Gregory A. Thompson, Beavercreek, OH (US); Glenn Leroy Thomas, Beavercreek, OH (US)

(73) Assignee: United States of America as represented by the Secretary of the Air Force, Washington, DC (US)

( * ) Notice: Subject to any disclaimer, the term of this patent is extended or adjusted under 35 U.S.C. 154(b) by 129 days.

(21) Appl. No.: 11/158,350

(22) Filed: Jun. 21, 2005

(51) Int. Cl.
  *G01N 7/00* (2006.01)
  *G01M 19/00* (2006.01)
(52) U.S. Cl. ..................... 73/866.4; 73/12.01
(58) Field of Classification Search ............... 73/865.4, 73/865.1, 865.3, 866.4, 12.01
See application file for complete search history.

(56) References Cited

U.S. PATENT DOCUMENTS

| | | | |
|---|---|---|---|
| 4,161,874 A | 7/1979 | Specker et al. | 73/12.01 |
| 4,691,556 A | 9/1987 | Mellander et al. | 73/12.01 |
| 5,546,609 A * | 8/1996 | Rush, III | 2/413 |
| 5,621,922 A * | 4/1997 | Rush, III | 2/422 |
| 5,978,972 A | 11/1999 | Stewart et al. | 2/422 |
| 6,691,585 B2 | 2/2004 | Ahn | 73/866.4 |
| 6,826,509 B2 * | 11/2004 | Crisco et al. | 702/141 |
| 2002/0060633 A1 * | 5/2002 | Crisco et al. | 340/669 |
| 2005/0177335 A1 * | 8/2005 | Crisco et al. | 702/141 |
| 2006/0038694 A1 * | 2/2006 | Naunheim et al. | 340/665 |

\* cited by examiner

*Primary Examiner*—Hezron Williams
*Assistant Examiner*—Tamiko Bellamy
(74) *Attorney, Agent, or Firm*—Steve Sayeedi; Chris Menke

(57) ABSTRACT

An anthropomorphic dummy head system is provided for measuring forces and moments applied to the back of the head and neck. The system includes a dummy head representing at least a portion of a human head and a force measuring device connected with the dummy head. The system also includes a skull cap attached to the force measuring device. The skull cap, representing a rear portion of a human head, may be free from direct attachment to the dummy head. The skull cap may further include a lower extension or nape extension configured to represent the back of a human neck.

20 Claims, 3 Drawing Sheets

ANTHROPOMORPHIC MANIKIN HEAD SKULL CAP LOAD MEASUREMENT DEVICE

RIGHTS OF THE GOVERNMENT

The invention described herein may be manufactured and used by or for the Government of the United States for all governmental purposes without the payment of any royalty.

FIELD OF THE INVENTION

The present invention relates generally to an anthropomorphic dummy head, and more specifically, to an anthropomorphic dummy head for use in measuring forces and moments exerted on the back of the head during trauma.

BACKGROUND OF THE INVENTION

Anthropomorphic dummies are used in research directed toward reducing injuries sustained during vehicle accidents and other traumatic impact events. Dummies are specifically manufactured to represent the appearance, weight, and center of gravity of a human being. Similarly, dummy heads, representing a human head, are used in research to study the effects of trauma on the head and brain. This research leads to the development of improved head safety gear and helps establish improved safety procedures.

The prior art teaches a number of devices to measure trauma to the head. For example, U.S. Pat. No. 4,161,874 to Specker et al. discloses a system for measuring head and back impact forces. The system has a movable plate member with an anthropometric dummy head and neck member secured to the plate member. Three force measuring cells are positioned in a horizontal plane and are connected between the movable plate member and three column members. Three vertical force measuring cells are positioned between a support plate and the movable plate member. High frequency response triaxial accelerometers are mounted at the center of gravity of the dummy head and neck member and on the movable plate member adjacent the attachment of the dummy head and neck member.

U.S. Pat. No. 4,691,556 to Mellander et al. discloses a test dummy head for measuring impact surface forces and pressures applied to the dummy head. The dummy head includes a pressure-sensing face incorporated to a dummy skull structure. Thin pressure-sensitive electric films are attached to the face. The films provide electrical signals representative of a time history of pressure or force applied up to 100 individual areas of the face. A pressurized calibration chamber is employed to simplify the calibration process.

Also, U.S. Pat. No. 6,691,585 to Ahn teaches an anthropomorphic dummy head for use in a vehicle crash test. The dummy head includes a skull member forming a shape of the head and an eye damage measuring part for estimating damage to an eye. The eye damage measuring part includes a housing disposed inside the skull member. The housing is closed and filled with compressible gas. The housing also includes a pressure sensor for detecting pressure inside the housing.

As described above, the prior art teaches a number of devices to detect forces on a dummy head. However, there exists a need for an anthropomorphic dummy head for measuring loads and moments on the back of the head, back of the neck, and other adjacent areas of the head.

SUMMARY OF THE INVENTION

The present invention provides a system for measuring loads and moments that are being exerted on the back of the head or neck from the external environment such as from a helmet system, blunt trauma, or from falls. In addition to measuring acceleration, the system provides information to isolate whether the acceleration is due to an inertial load or an impact event.

In accordance with one aspect of the invention, there is provided an anthropomorphic dummy head system. The system includes a dummy head representing at least a portion of a human head and a force acquisition device connected with the dummy head. The system also includes a skull cap attached to the force acquisition device. The skull cap is dimensioned and configured to represent a rear portion of the dummy head or human head.

The dummy head may include a base structure and a headform material attached to the base structure. The headform material is configured to represent at least a portion of a human head. An interface plate is connected with a rear section of the base structure, and the force acquisition device is attached to the interface plate. Ballast may be included within the dummy head providing weight to the system to thereby generally match the weight and center of gravity of a human head.

In a related aspect of the invention, the skull cap is free from direct attachment to the dummy head or any other component of the system except for the data acquisition system. Also, the skull cap may include a lower extension or nape portion configured to represent the back of a human neck. The skull cap may be made of metallic, polymeric, ceramic, and composite material or combinations thereof.

In accordance with a further aspect of the present invention, the anthropomorphic dummy head system includes a helmet positioned over the dummy head and skull cap. A variety of helmets may be placed on the dummy head to include a flight helmet for aircrew, a racing helmet for race car drivers, a bike helmet for motorcycle riders, or a protective helmet for athletes or industrial workers. When a force is applied to the helmet by the external environment, such as a head rest, ejection seat, the ground, etc., the data acquisition system measures the forces and moments exerted on the skull cap and the nape portion of the skull cap.

The data acquisition system may be a standard load cell, like a 6-axis automotive crash testing load cell. The load cell measures forces and/or moments applied against the back of the head and nape of the dummy head. A microprocessor may be connected with the force acquisition device for manipulating the data.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE INVENTION

Figure 1:
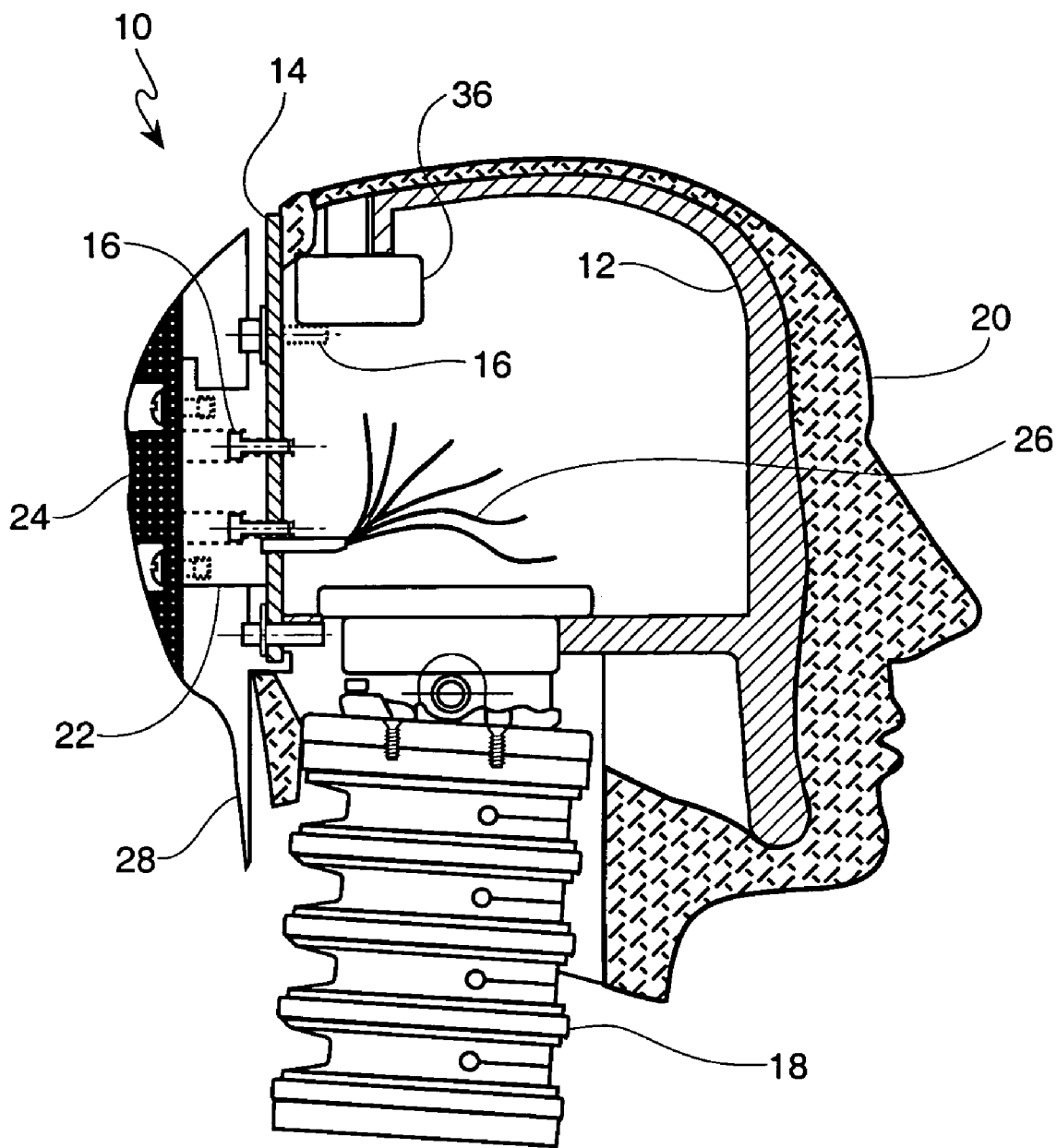
FIG. 1 is a cross-sectional view an anthropomorphic dummy head of the present invention.

For convenience, the same or equivalent elements in the various embodiments of the invention illustrated in the drawings have been identified with the same reference numerals. Further, in the description that follows, any reference to either orientation or direction is intended primarily for the convenience of description and is not intended in any way to limit the scope of the present invention thereto. Finally, any reference to a particular application, such as force and moment measurement during aircraft ejection, is simply used for convenience as one example of a possible use for the invention and is not intended to limit the scope of the present invention thereto.

The anthropomorphic dummy head system of the present invention provides for the measurement for forces and moments that are being applied to the back of the head or the nape. Such forces and moments may originate from the external environment such as from a helmet system, blunt trauma, or from falls. In addition to measuring acceleration, the system provides data to isolate whether the acceleration is due to an inertial load or and impact event.

Figure 2:
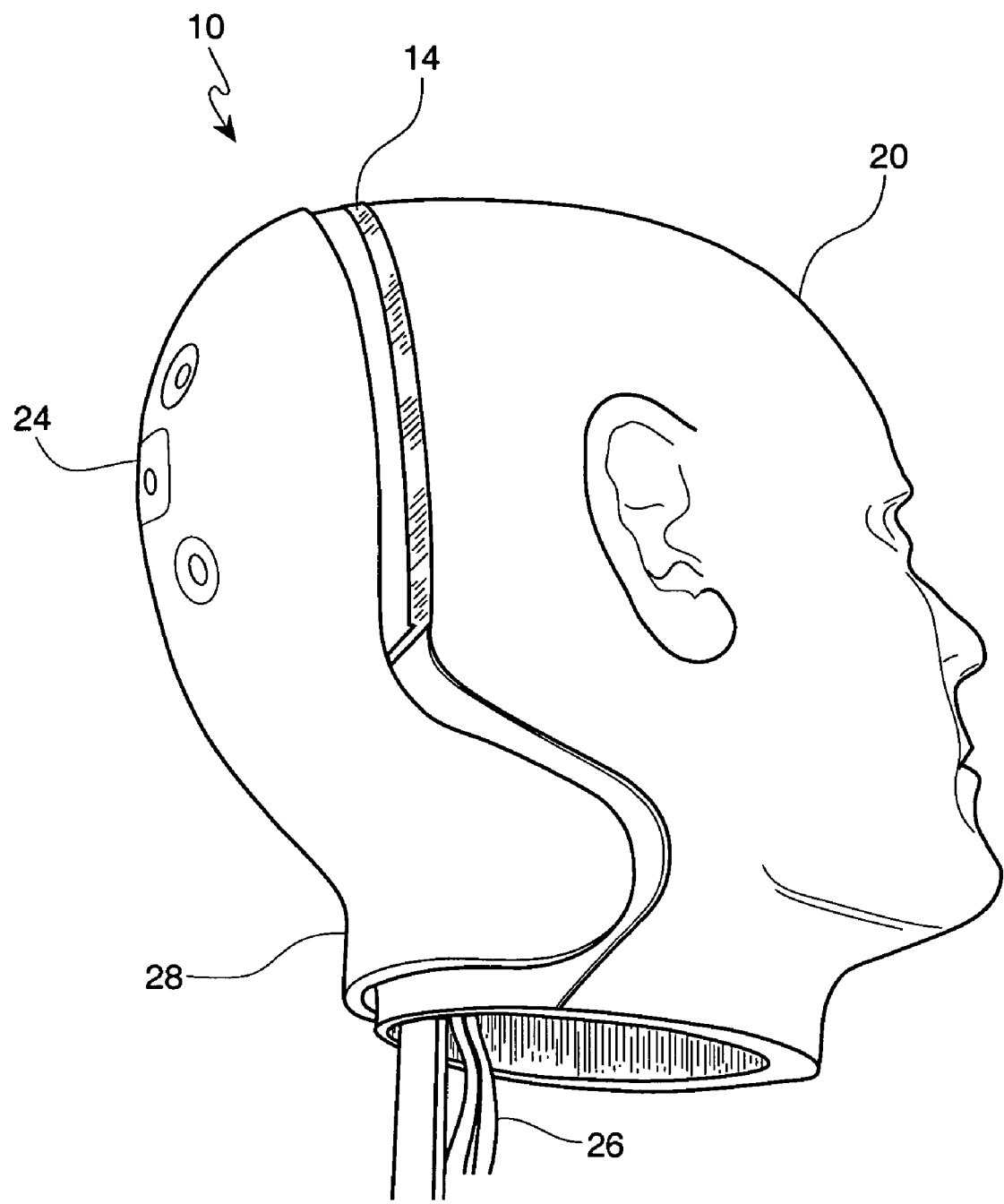
FIG. 2 is a perspective view of the dummy head.
Figure 3:
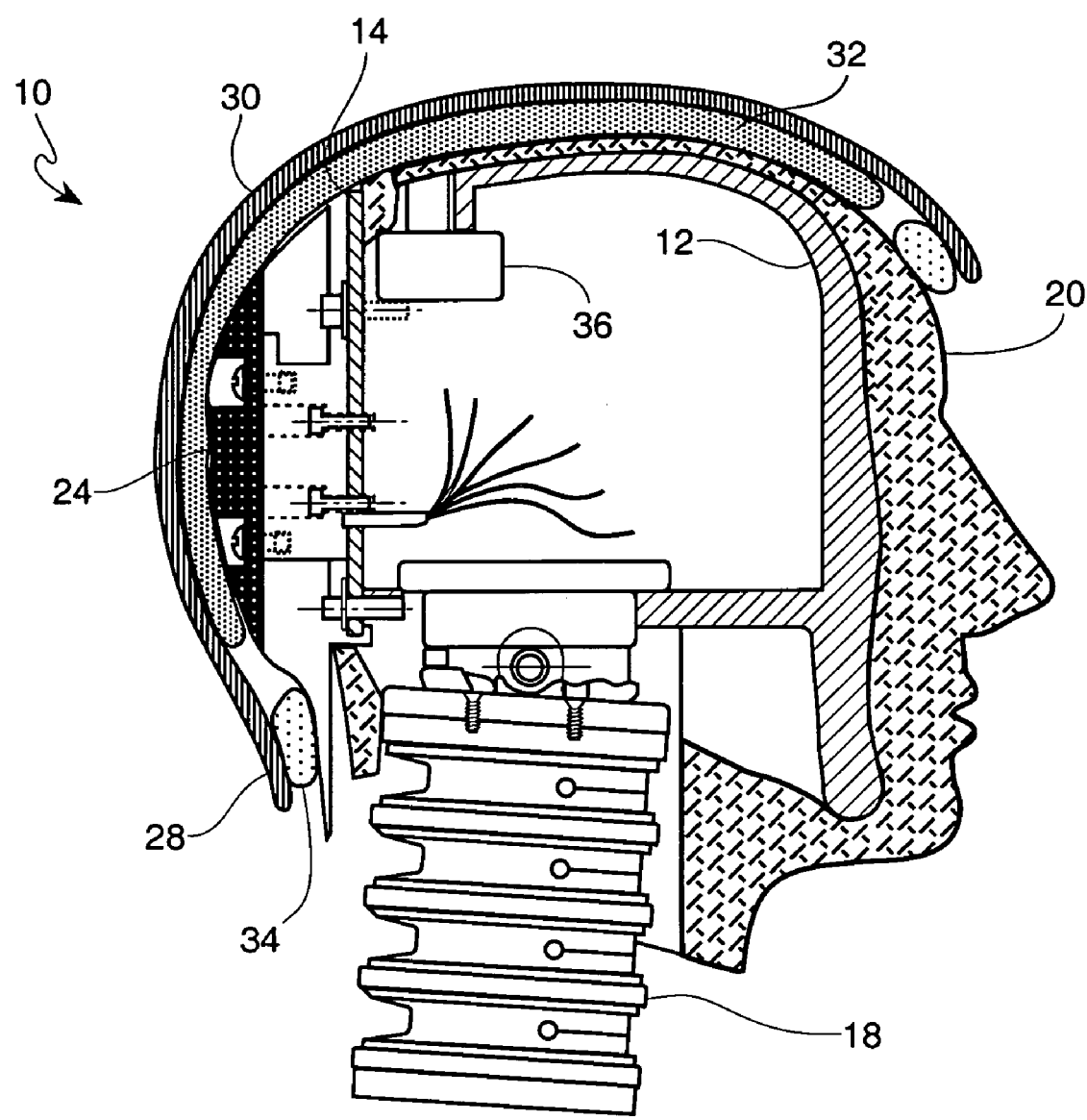
FIG. 3 is a cross-sectional view of the dummy head with a helmet thereon.

FIGS. 1–3 illustrate an exemplary embodiment of the present invention. As shown in FIG. 1, the anthropomorphic dummy head system 10 includes an internal base structure 12 and a support column 18 attached to the base structure 12. The support column 18 may be rigidly connected with the base structure 12 by way of welding, screwing, bolting, etc. Alternatively, the support column 18 and base structure 12 may be pivotally attached to each other to thereby emulate the pivotal connection of a human neck and head. Attached to the exterior surface of the internal base structure is headform material 20 configured and dimensioned to represent a human face and other features such as a jaw, ears, etc.

The internal base structure 12, support column 18, and headform material 20 previously described may be part of a Hybrid II or Hybrid III test dummy. These test dummies are generally manufactured to represent $5^{th}$ percentile, $50^{th}$ percentile, and $95^{th}$ percentile male and female humans. Other test dummies representing children are also available. Generally, the head of an adult Hybrid test dummy weighs approximately 8 to 12 lbs. and has a circumference of about 21 to 23 inches, a breadth of approximately 5 to 7 inches, and a depth/length of about 6.5 to 7.5 inches. In the present invention, a Hybrid II dummy head was modified and used to measure loads and moments on the back of the head. However, it should be understood that any adult, child, male, or female dummy head may be modified as described herein.

The anthropomorphic dummy head system 10 further includes an adapter or interface plate 14 connected with a rear portion of the internal base structure 12. The adapter plate 14 may be made of a metallic material, such as aluminum, and may be welded, latched, or screwed to the base structure 12. In one embodiment, the plate 14 and base structure 12 are connected with one or more bolts 16. A data acquisition system 22 is connected to the adapter plate 14, preferably with one or more bolts 16. The data acquisition system 22 may be any device capable of measuring forces and/or moments. In an exemplary embodiment, the data acquisition system 22 is a 6-axis load cell, like a standard automotive load cell used in crash testing. For example, an automotive CRABI load cell may utilized with the present invention. A plurality of wires 26 extending from the data acquisition system 22 may be connected with a microprocessor for recording, manipulating, and displaying data.

Referring to FIGS. 1 and 2, a dorsal skull cap 24 is attached to the data acquisition system 22. The dorsal skull cap 24 is generally a shaped plate configured and dimensioned to represent the back portion of the human skull or dummy head. The skull cap 24 is unattached or free from attachment with the adapter plate 14 or other component of the dummy head, except the data acquisition system 22. In this configuration, the skull cap 24 transfers external forces apply against the cap 24 to the data acquisition system 22 for force and moment measurement. The dorsal skull cap 24 may be made of metallic, polymeric, or ceramic, material, but preferably, the cap 24 is made from composite material. Furthermore, the dorsal skull cap 24 includes a lower, flared-out extension or a nape portion 28. The nape portion 28 of the cap 24 represents an area of the neck below the occipital bone of the human skull, and more particularly, an area below the external occipital protuberance. The dorsal skull cap 24 with the nape portion 28 provides a contact surface to which forces may be applied to measure loads and moments experienced by the back of the head and neck.

FIG. 3 illustrates the anthropomorphic dummy head system 10 with a helmet 30 thereon. The helmet 30 includes padding 32 positioned within the helmet 30 and in contact with the dummy head. The helmet 30 also includes a nape strap 34 which is located adjacent the nape portion 28 of the dorsal skull cap 24. The nape strap 34 transfers forces applied against the helmet into the nape portion 28 of the cap 24 for measuring loads and moments experienced by the back of the neck. It is contemplated that any type of helmet may be utilized with the dummy head system of the present invention. For example, the helmet may be a flight helmet for aircrew, a racing helmet for race car drivers, a bike helmet for motorcycle riders, or a protective helmet for athletes or industrial workers.

Also shown in FIG. 3 is head ballast 36. The ballast 36 is added to the internal base structure 12 to bring the weight and center of gravity of the head to generally similar specifications as a standard dummy head or human head. Attachment of the dorsal skull cap 24 and adapter plate 14 to the base structure 12 may change the weight of the dummy head; therefore, the ballast 36 brings the dummy head back to the proper weight and center of gravity.

The anthropomorphic dummy head system has a variety of applications. For example, the system may be used to measure the forces and moments being applied to the back of the head and neck from an aircrew member's helmet during an aircraft ejection, during impact with the seat headrest, and/or during impact with the ground or ground object upon a parachute landing. Also, ejection testing may be used to measure helmet lift. The configuration of the dorsal skull cap with the nape portion allows for measurement of loads and moments exerted by the flight helmet and nape strap. Subsequent analysis of the data measured by the load cell during the test can provide an indication of potential injuries to humans or provide comparative data on different helmets, ejection seats, or safety systems.

Other applications of the system include measuring forces on the back of the head and neck during sled impact testing, windblast testing to measure helmet lift and drag forces, and helmet pull testing for measuring helmet strap load distribution. Furthermore, the system may be used in the evaluation of commercial and industrial helmet systems (such as motorsports, motorcycles, bicycles, hardhats, etc.) and in the evaluation of the crashworthiness of vehicles. The system may also be used to measure head impact forces during automotive crash testing (rearward impact, rollover, etc.) and during falls from objects such as ladders. The data obtained can then be utilized to assess the probability of injury to the head or to conduct comparison tests of multiple devices.

While various descriptions of the present invention are described above, it should be understood that the various features can be used singularly or in any combination thereof. Therefore, this invention is not to be limited to only the specific embodiments depicted herein. Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An anthropomorphic dummy head system comprising:
a dummy head configured and dimensioned to represent at least a portion of a human head;
a force measuring device connected with the dummy head; and
a skull cap attached to the force measuring device, the skull cap dimensioned and configured to represent a rear portion of a human head.

2. The system of claim 1, wherein the skull cap is free from direct attachment to the dummy head.

3. The system of claim 2, wherein the skull cap includes a lower extension configured to represent the back of a human neck.

4. The system of claim 3, further including ballast connected with the dummy head, the ballast providing weight to the system to thereby generally match the weight of a human head.

5. The system of claim 4, wherein the skull cap includes composite material.

6. The system of claim 1, wherein the force measuring device is a load cell.

7. The system of claim 6, wherein the load cell is a 6-axis load cell.

8. An anthropomorphic dummy head system comprising:
a base structure;
a headform material attached to the base structure and configured to represent at least a portion of a human head;
an interface plate connected with a rear section of the base structure;
a force acquisition device connected with the interface plate; and
a skull cap attached to the force acquisition device, the skull cap dimensioned and configured to represent a rear portion of a human head.

9. The system of claim 8, wherein the skull cap is free from direct attachment with the interface plate and base structure.

10. The system of claim 9, wherein the skull cap include a nape portion.

11. The system of claim 10, wherein the force acquisition device measures a force applied to the skull cap.

12. The system of claim 11, further including a microprocessor connected with the force acquisition device.

13. An anthropomorphic dummy head system comprising:
a dummy head configured and dimensioned to represent at least a portion of a human head;
a load cell connected with the dummy head;
a skull cap attached to the load cell, the skull cap dimensioned and configured to represent a rear portion of a human head; and
a helmet positioned over the dummy head and skull cap.

14. The system of claim 13, wherein an interior surface of the helmet contacts the skull cap.

15. The system of claim 14, wherein the load cell measures a force applied to the helmet.

16. The system of claim 15, wherein the force is applied to the back of the helmet.

17. The system of claim 13, wherein the skull cap includes a nape portion.

18. The system of claim 17, wherein a strap of the helmet contacts the nape portion of the skull cap.

19. The system of claim 18, wherein the load cell measures a force applied to the strap of the helmet.

20. The system of claim 19, wherein the helmet is a flight helmet.

* * * * *